(12) United States Patent
Orme et al.

(10) Patent No.: US 6,903,099 B2
(45) Date of Patent: Jun. 7, 2005

(54) CONDENSED PYRAZINDIONE DERIVATIVES

(75) Inventors: Mark W. Orme, Seattle, WA (US); Jason Scott Sawyer, Indianapolis, IN (US); Lisa M. Schultze, Woodinville, WA (US)

(73) Assignee: Lilly Icos LLC, Wilmington, DE (US)

( * ) Notice: Subject to any disclaimer, the term of this patent is extended or adjusted under 35 U.S.C. 154(b) by 0 days.

(21) Appl. No.: 10/297,735

(22) PCT Filed: May 15, 2001

(86) PCT No.: PCT/US01/15550

§ 371 (c)(1),
(2), (4) Date: Dec. 6, 2002

(87) PCT Pub. No.: WO02/00657

PCT Pub. Date: Jan. 3, 2002

(65) Prior Publication Data

US 2003/0181457 A1 Sep. 25, 2003

Related U.S. Application Data

(60) Provisional application No. 60/214,284, filed on Jun. 26, 2000.

(51) Int. Cl.$^7$ ........................ A61K 31/50; C07D 241/36
(52) U.S. Cl. ........................ 514/250; 544/343
(58) Field of Search ........................ 544/343; 514/250

(56) References Cited

FOREIGN PATENT DOCUMENTS

| WO | WO 95/19978 | 7/1995 |
|---|---|---|
| WO | WO 97/03675 | 2/1997 |

OTHER PUBLICATIONS

Kaplan et al, "Safety and Efficacy of Sildenafil in Postmenopausal Women with Sexual Dysfunction" Urology, vol. 53(3), pp. 481–486 (1999).*
Berman, M.D. and Goldstein, M.D. Letters to the editor, Urology, vol. 54(3), pp. 578–579, (1999).*
West, Anthony R. "Solid State Chemistry and its Applications" Wiley, New York, pp. 358 and 365 (1988).*
Hawley's Condensed Chemical Dictionary, 12th ed., Richard J. Lewis, Sr. , © 1993 by Van Nostrand Reinhold. p. 594.*
Concise Chemical Dictionary, edited by Drs. Hans–Dieter Jakubke and Hans Jeschkeit, © 1993 by Walter de Gruyter & Co., p. 490.*
McGraw–Hill Dictionary of Chemical Terms, 3rd ed. edited by Sybil P. Parker, © 1984 McGraw–Hill, Inc., p. 200.*

* cited by examiner

Primary Examiner—James O. Wilson
Assistant Examiner—Zachary C. Tucker
(74) Attorney, Agent, or Firm—Marshall, Gerstein & Borun LLP

(57) ABSTRACT

Compounds of the general structural formula (I) and use of the compounds and salts and solvates thereof, as therapeutic agents.

14 Claims, No Drawings

CONDENSED PYRAZINDIONE DERIVATIVES

CROSS REFERENCE TO RELATED APPLICATION

This is the U.S. national phase application of International Application No. PCT/US01/15550, filed May 15, 2001, which claims the benefit of U.S. provisional patent application Ser. No. 60/214,284, filed Jun. 26, 2000.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

DETAILED DESCRIPTION OF THE INVENTION

The present invention is directed to compounds having the general structural formula (I):

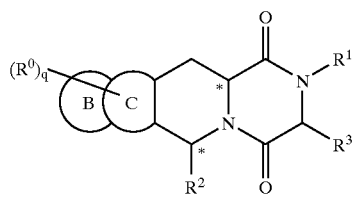

wherein $R^0$, independently, is selected from the group consisting of halo and $C_{1-6}$alkyl;

$R^1$ is selected from the group consisting of hydrogen, $C_{1-6}$alkyl, $C_{2-6}$alkenyl, $C_{2-6}$alkynyl, $haloC_{1-6}$-alkyl, $C_{3-8}$cycloalkyl, $C_{3-8}$cycloalkyl$C_{1-3}$alkyl, aryl-$C_{1-3}$alkyl, and heteroaryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

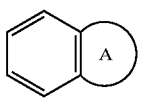

wherein the fused ring A is a 5- or 6-membered ring, saturated or partially or fully unsaturated, and comprises carbon atoms and optionally one or two heteroatoms selected from oxygen, sulfur, and nitrogen;

$R^3$ is hydrogen or $C_{1-3}$alkyl, or $R^1$ and $R^3$ together form a 3- or 4-membered alkyl or alkenyl component of a 5- or 6-membered heterocyclic ring;

rings B and C form an optionally substituted fused ring structure selected from the group consisting of

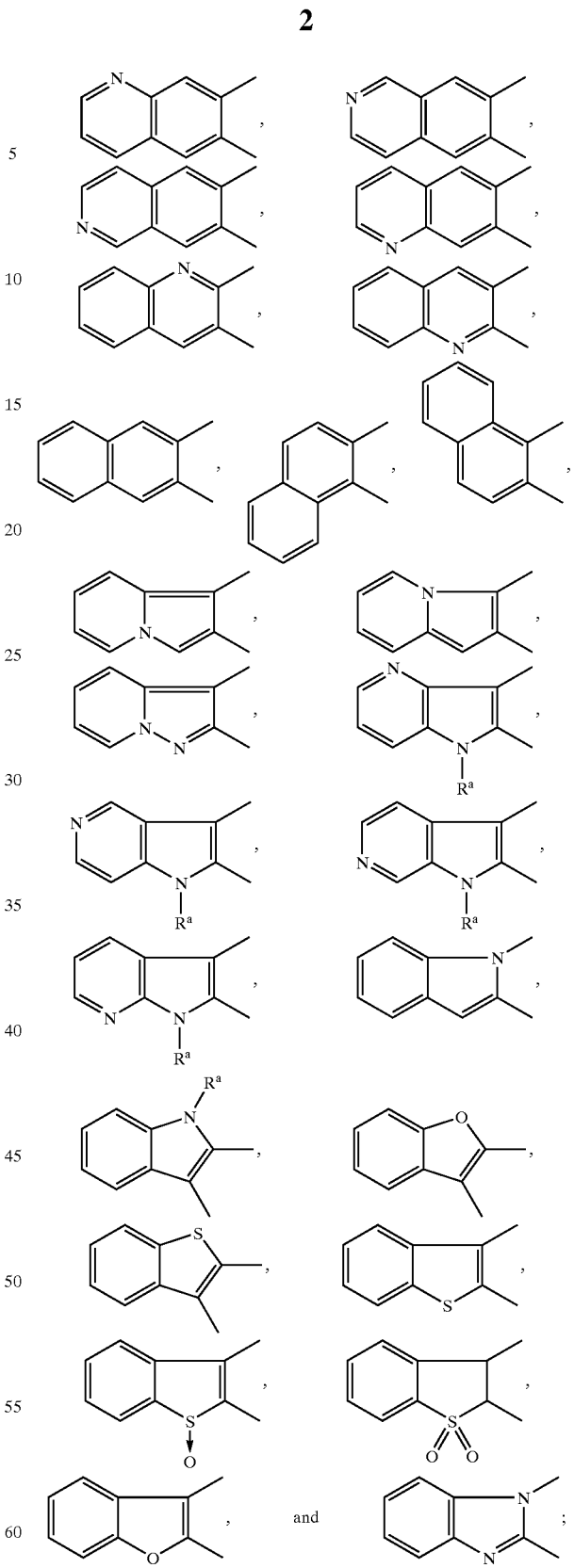

$R^a$ is selected from the group consisting of hydrogen, $C_{1-6}$alkyl, $C_{3-8}$cycloalkyl, aryl, aryl$C_{1-3}$-alkyl, $C_{1-3}$alkylenearyl; and q is 0, 1, 2, 3, or 4;

pharmaceutically acceptable salts and hydrates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl.

The term "cycloalkyl" is defined as a cyclic $C_3$–$C_8$ hydrocarbon group, e.g., cyclopropyl, cyclobutyl, cyclohexyl, and cyclopentyl.

The terms "alkenyl" and "alkynyl" are defined similarly as alkyl, except the group has a carbon-carbon double bond or a carbon-carbon triple bond, respectively.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, alkyl, halo, hydroxy, hydroxyalkyl, alkoxy, alkoxyalkyl, haloalkyl, nitro, amino, alkylamino, acylamino, alkylthio, alkylsulfinyl, and alkylsulfonyl. Examples of aryl groups include, but are not limited to, phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "hydroxy" is defined as —OH.

The term "hydroxyalkyl" is defined as a hydroxy group appended to an alkyl group.

The term "alkoxy" is defined as —OR, wherein R is alkyl.

The term "alkoxyalkyl" is defined as an alkyl group wherein a hydrogen has been replaced by an alkoxy group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, where R is alkyl.

The term "alkylsulfonyl" is defined as R—SO$_3$, where R is alkyl.

The term "nitro" is defined as —NO$_2$.

The term "cyano" is defined as —CN.

With respect to $R^0$, the $R^0$ substituents can be present on the B ring or the C ring. If more than one $R^0$ is present, the $R^0$ substituents can be on one ring or can be on both rings.

In a preferred embodiment, $R^2$ is the optionally substituted bicyclic ring system

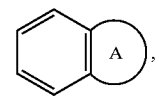

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

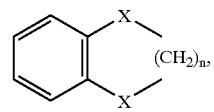

wherein n is an integer 1 or 2, and X, independently, are $C(R^a)_2$, O, S, or $NR^a$. The bicyclic ring comprising the $R^2$ substituent typically is attached to the rest of the molecule by a phenyl ring carbon atom.

In a preferred group of compounds of formula (I), $R^2$ is represented by an optionally substituted bicyclic ring

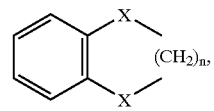

wherein n is 1 or 2, and X, independently, are CH$_2$ or O. Especially preferred $R^2$ substituents include

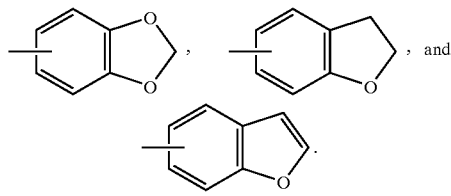

Within this particular group of compounds, nonlimiting examples of substituents for the bicyclic ring include halogen (e.g., chlorine), $C_{1-3}$alkyl (e.g., methyl, ethyl, or i-propyl), OR$^a$ (e.g., methoxy, ethoxy, or hydroxy), CO$_2$R$^a$, halomethyl or halomethoxy (e.g., trifluoromethyl or trifluoromethoxy), cyano, nitro, and N(R$^a$)$_2$.

An especially preferred subclass of compounds within the general scope of formula (I) is represented by compounds of formula (II)

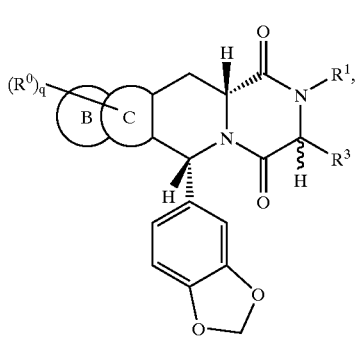

(II)

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, chronic obstructive pulmonary disease, congestive heart failure, malignant hypertension, pheochromocytoma, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, myocardial infarction, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder, also termed female sexual arousal disorder. Female sexual arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female sexual arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and sexual arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female sexual arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, malignant hypertension, pheochromocytoma, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, peptic ulcer, benign prostatic hypertrophy, male and female erectile dysfunction, or diseases-characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic-solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts retain the biological effectiveness and properties of the free acids, and are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition, comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or sexual arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the synthetic methods below, $R^0$, $R^1$, $R^2$, and $R^3$ are as defined in structural formula (I) above. For example, compounds of formula (I) can be prepared by the methods set forth in Daugan U.S. Pat. No. 5,859,006, incorporated herein by reference, utilizing the appropriate starting materials. Protecting compounds and protecting groups, like benzyl chloroformate and trichloroethyl chloroformate, that are well known to persons skilled in the art, for example, see T. W. Greene et al. "Protective Groups in Organic Synthesis, Third Edition," John Wiley and Sons, Inc., NY, N.Y. (1999), also can be utilized in the synthesis of compounds of structural formula (I).

Compounds of formula (I) can be converted to other compounds of formula (I). Thus, for example, when $R^2$ is a substituted benzene ring, it is possible to prepare another suitably substituted compound of formula (I). Examples of appropriate interconversions include, but are not limited to, nitro to amino, $OR^a$ to hydroxy by suitable reducing means (e.g., using a suitable agent, such as $SnCl_2$ or a palladium catalyst, such as palladium-on-carbon), or amino to substituted amino, such as acylamino or sulphonylamino, using standard acylating or sulfonylating conditions. In cases wherein $R^2$ represents a substituted bicyclic system, suitable interconversion can involve removal of a substituent, such as by treatment with a palladium catalyst whereby, for example, a benzyl substituent is removed from a suitable bicyclic system.

Compounds of formula (I) can be prepared by the method above as individual stereoisomers from the appropriate stereoisomer or as a racemic mixture. Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following abbreviations are used hereafter in the accompanying examples: rt (room temperature), min (minute), h (hour), g (gram), mmol (millimole), m.p. (melting point), eq (equivalents), L (liter), mL (milliliter), μL (microliters), Me (methyl), Bn (benzyl), DMSO (dimethyl sulfoxide), $CH_2Cl_2$ (dichloromethane), IPA (isopropyl alcohol), TFA (trifluoroacetic acid), TPAP (tetrapropylammonium perruthenate), $SOCl_2$ (thionyl chloride), $Et_3N$ (triethylamine), $CH_3NH_2$ (methylamine), EtOAc (ethyl acetate), EtOH (ethanol), DMF (dimethyl formamide), $CHCl_3$ (chloroform), EtOAc (ethyl acetate), MeOH (methanol), and THF (tetrahydrofuran).

PREPARATION OF EXAMPLE 1

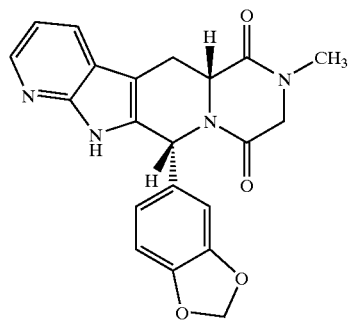

Example 1

Example 1 was prepared from Intermediates 1–3 as depicted in the following synthetic scheme. Intermediate 1 was prepared from DL-7-azatryptophan, a commercially available compound from Aldrich Chemical Co., Milwaukee, Wis.

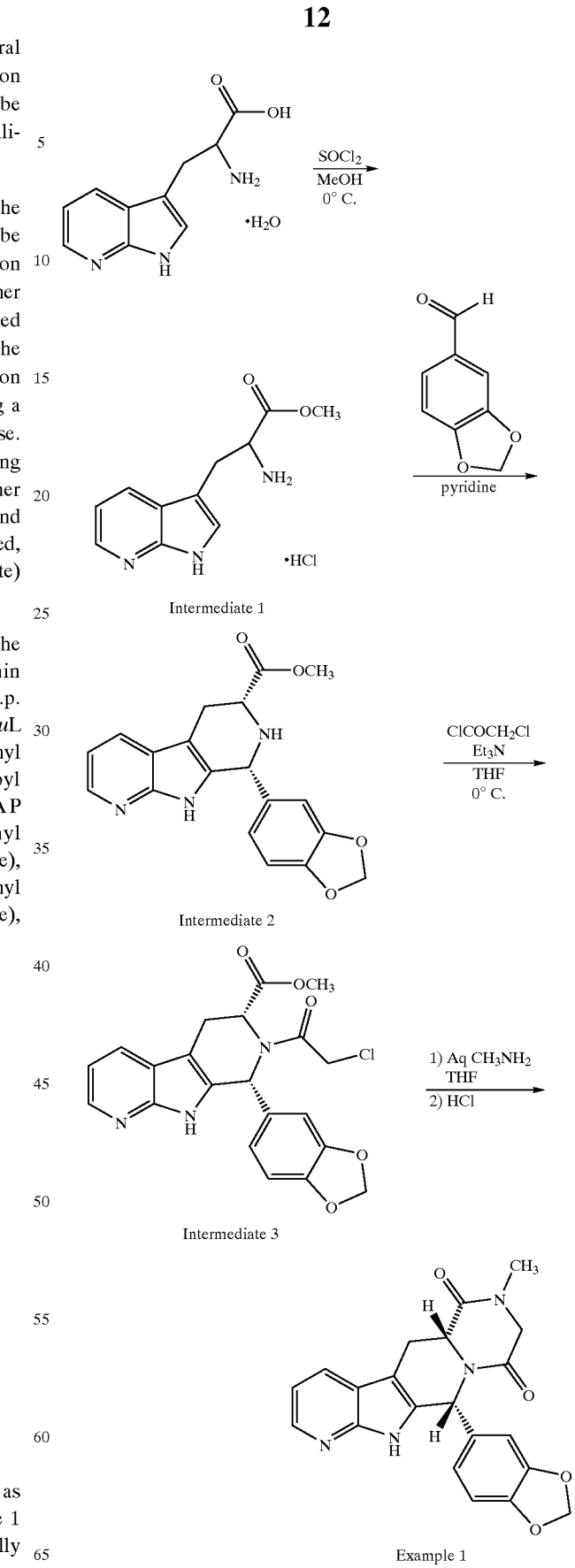

Intermediate 1

Preparation of DL-7-Azatryptophan Methyl Ester Monohydrochloride

Thionyl chloride (1.74 g, 1.1 mL, 14.6 mmol) was added dropwise to a suspension of DL-7-azatryptophan monohydrate (1.00 g, 4.87 mmol) in anhydrous methanol (40 mL) at 0° C. under a nitrogen blanket. The mixture was warmed slowly to room temperature and stirred for 24 hours. The methanol was removed under reduced pressure to provide a white solid. Analysis of the resulting solid by $^1$H NMR showed the solid to be a mixture of starting material and Intermediate 1. The thionyl chloride treatment was repeated an additional time as described above to provide a white solid (1.39 g, 100%). $^1$H NMR (300 MHz, CDCl$_3$): δ 12.05 (s, 1H), 8.54 (bs, 2H), 8.31 (d, J=4.3 Hz, 1H), 8.18 (d, J=8.0 Hz, 1H), 7.47 (d, J=2.1 Hz, 1H), 7.24 (dd, J=5.0 Hz, J=7.8 Hz, 1H), 4.34 (m, 1H), 3.70 (s, 3H), 3.33 (d, J=6.1 Hz, 2H).

Intermediate 2

Preparation of a (+/−)-cis-β-Carboline

A suspension of Intermediate 1 (1.39 g, 5.44 mmol) and piperonal (1.06 g, 7.07 mmol) in pyridine (35 mL) was warmed to 100° C. and stirred for 5 hours under a nitrogen blanket. The resulting brown suspension was cooled to room temperature and filtered to remove unreacted starting material. The filtrate was concentrated in vacuo and was purified by column chromatography (silica gel, 1–20% MeOH/CH$_2$Cl$_2$) to give 0.34 g of a white solid. The solid was repurified by column chromatography (silica gel, 0–4% MeOH/CHCl$_3$), and was triturated with MeOH to provide 0.31 g (16.4%) of the cis product, which was approximately 94% pure by $^1$H NMR analysis. TLC R$_f$ (5% MeOH/CH$_2$Cl$_2$)=0.51; $^1$H NMR (306 MHz, CDCl$_3$): δ 10.99 (s, 1H), 8.10 (dd, J=1.4 Hz, J=4.7 Hz, 1H), 7.86 (d, J=6.75, 1H), 7.00 (dd, J=4.7 Hz, J=7.8 Hz, 1H), 6.81–6.90 (m, 3H), 6.00 (d, J=1 Hz, 1H), 5.16 (m, 1H), 3.82–3.89 (m, 1H), 3.70 (s, 3H), 2.98–3.07 (m, 1H), 2.77–2.87 (m, 1H), 2.68–2.73 (m, 1H); MS (API) m/z 352 (M+H). The trans carboline also was eluted from the column in impure form: TLC R$_f$ (5% MeOH/CH$_2$Cl$_2$)=0.40.

Intermediate 3

Preparation of a (+/−)-cis-2-Chloroacetyl-β-carboline

Chloroacetyl chloride (0.11 mL, 1.34 mmol) was added dropwise to a mixture of Intermediate 2 (0.31 g, 0.89 mmol) and triethylamine (0.5 mL, 3.6 mmol) in CH$_2$Cl$_2$ (25 mL) at 0° C. under a nitrogen blanket. The resulting mixture was warmed to room temperature and stirred for about 1.5 hours. The reaction was quenched with 1 N HCl (2 mL), and was diluted with CH$_2$Cl$_2$ (25 mL) and water (10 mL). The layers were separated. The organic phase was washed with saturated sodium bicarbonate (NaHCO$_3$) and brine, then dried over anhydrous sodium sulfate (Na$_2$SO$_4$). Filtration and concentration in vacuo yielded Intermediate 3 as a greenish foam (0.39 g), which was used without purification in the next step: TLC R$_f$ (10% MeOH/CH$_2$Cl$_2$)=0.58; MS (API) m/z 428 (M+H).

Example 1

Preparation of (+/−,cis)-10-Benzo[1,3]dioxol-5-yl-7-methyl-5,5a,7,8,10,11-hexahydro-1,7,9a,11-tetraazabeno[β]fluorene-6,9-dione A mixture of the crude Intermediate 3 (0.38 g, 0.89 mmol), 40% methylamine in water (1.47 mL, 17.1 mmol), THF (40 mL), and MeOH (10 mL) was heated at 40° C. under a nitrogen blanket for 2.5 hours. The resulting solution was cooled to room temperature, then acidified with concentrated hydrochloric acid (HCl). The resulting mixture was diluted with CH$_2$Cl$_2$ (25 mL), the layers were separated, and the organic phase was washed with water (10 mL) and brine (10 mL). The organic layer was dried over anhydrous Na$_2$SO$_4$, filtered and concentrated in vacuo. The product was purified by column chromatography (silica gel, 0–5% MeOH/CH$_2$Cl$_2$) to provide a white solid (0.20 g, 57.5% over two steps) after drying at 45° C. under vacuum. The product was contaminated with approximately 10% of the trans isomer: mp 262–276° C.; TLC R$_f$ (10% MeOH/CH$_2$Cl$_2$)= 0.45; $^1$H NMR (300 MHz, DMSO-d$_6$): δ 11.65 (s, 1H), 8.15 (dd, J=1.5 Hz, J=4.7 Hz, 1H), 8.00 (dd, J=1.2 Hz, J=7.8 Hz, 1H), 7.05 (dd, J=4.8 Hz, J=7.9 Hz, 1H), 6.90 (s, 1H), 6.82–6.90 (m, 2H), 6.13 (s, 1H), 5.93 (s, 2H), 4.42 (dd, J=4.4 Hz, J=11.8 Hz, 1H), 4.19 (d, J=16.6 Hz, 1H), 3.96 (d, J=17.2 Hz, 1H), 3.55 (dd, J=4.51, J=16.0 Hz, 1H), 2.92–3.01 (m, 4H), 3.94 (s, 3H); MS (API) m/z 391 (M+H); [α]$_D^{25° C.}$=no observed rotation (c=0.15, DMSO). Anal. Calcd. for C$_{21}$H$_{18}$N$_4$O$_4$·0.7 H$_2$O: C, 62.59; H, 4.85; N, 13.90. Found: C, 62.61; H, 4.71; N, 13.88. The relative stereochemistry of the major product was confirmed to be the cis isomer by NOE difference experiments (DMSO-d$_6$): positive NOE enhancements from the C5a proton at 4.42 ppm to the C10 proton at 6.13 ppm.

PREPARATION OF EXAMPLE 2

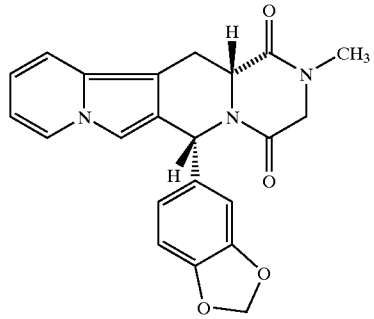

Example 2

Example 2 can be prepared from the indolizine-substituted alanine Intermediate 4, the synthesis of which is disclosed in M. Cardellini et al., *Ann. Chim. (Rome)*, 58(11), pages 1206–1213 (1968), and P. Gmeiner et al., *Arch. Pharm.*, 321(9), pages 505–507 (1988). The following is an envisioned synthetic route to Example 2.

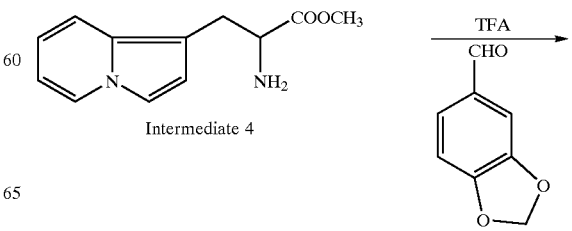

Intermediate 4

Example 3

PREPARATION OF EXAMPLE 4

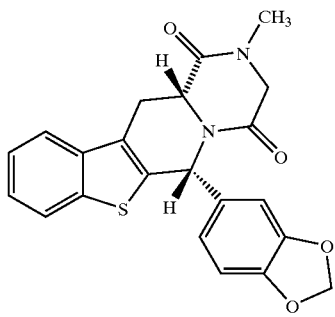

Example 4

Example 4 was prepared from Intermediates 6–8 as depicted in the following synthetic scheme. Intermediate 6 was prepared from (R)-α-amino-3-[1]benzothiophene-3-ylpropionic acid, commercially available from Aldrich Chemical Co., Milwaukee, Wis. Aspects of the following sequence are disclosed in H. Kawakubo, *J. Med. Chem.*, 36, pages 3526–3532 (1993) and H. Kawakubo et al., *J. Med. Chem.*, 33, pages 3110–3116 (1990).

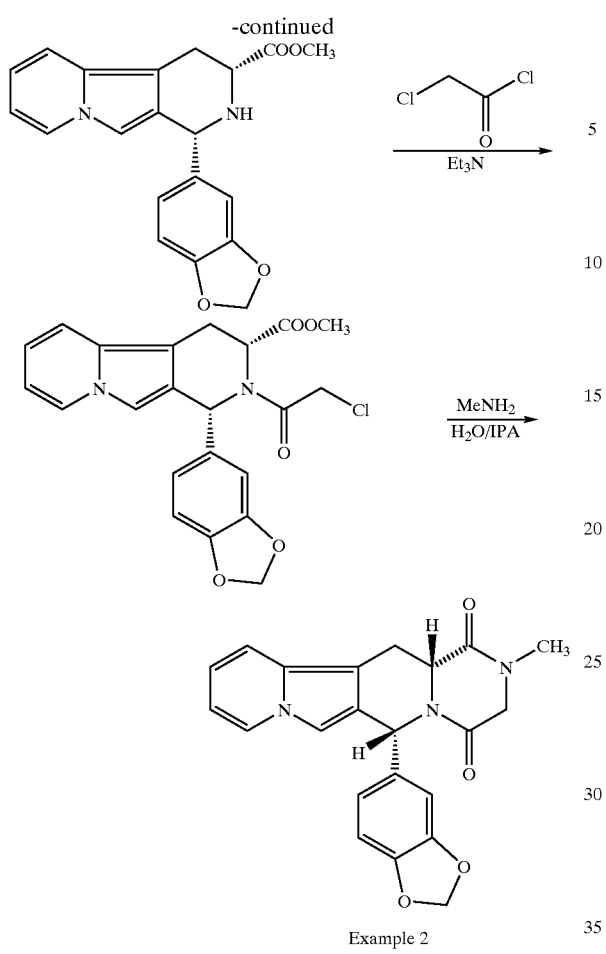

Example 2

PREPARATION OF EXAMPLE 3

The following Example 3 can be prepared by the same envisioned synthetic route as Example 2, starting with the azaindolizine-substituted alanine Intermediate 5.

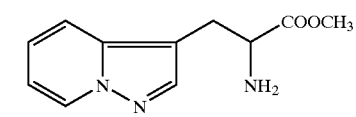

Intermediate 5

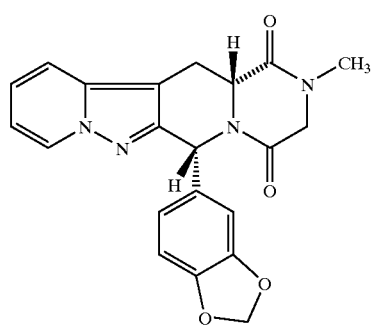

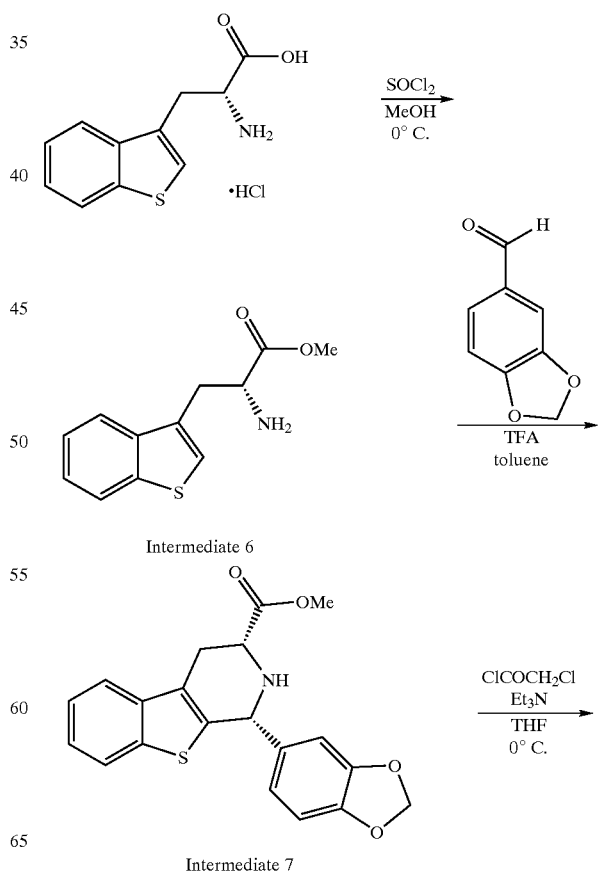

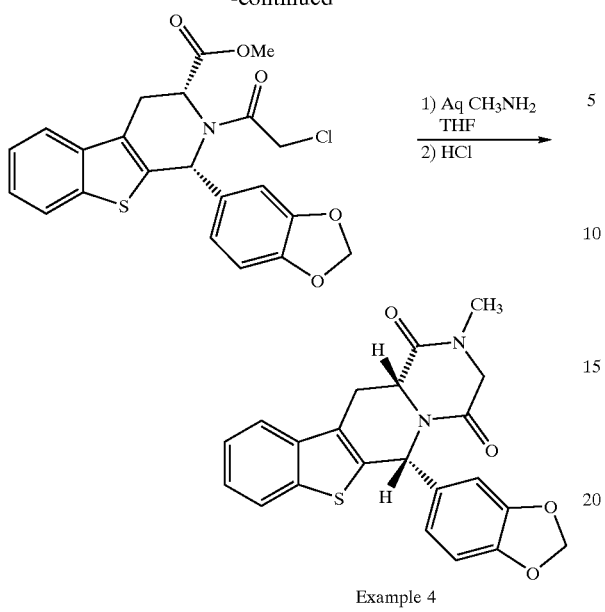

Example 4

Intermediate 6

Preparation of (R)-α-Amino-3-[1]benzothiophene-3-ylpropionic Acid Methyl Ester Thionyl chloride (2.69 g, 22.6 mmol) was added dropwise to a suspension of (R)-α-amino-3-[1]benzothiophene-3-ylpropionic acid (1.00 g, 4.52 mmol) in anhydrous MeOH (20 mL) at 0° C. under a nitrogen blanket. The mixture was warmed slowly to room temperature and stirred for a total of 24 hours. The solvent was removed under reduced pressure to provide a pale yellow solid. The resulting residue was dissolved in MeOH (10 mL), then diluted with 1:1 $CH_2Cl_2$:saturated $NaHCO_3$ (50 mL). The layers were separated, and the aqueous layer was back-extracted with $CH_2Cl_2$ (25 mL). The combined organic phases were washed with water, saturated sodium chloride (NaCl), dried over anhydrous $Na_2SO_4$, filtered, and concentrated to provide a pale brown oil (1.08 g, 100%): TLC $R_f$ (90:10:1; $CH_2Cl_2$:EtOAc:MeOH)=0.34; $^1H$ NMR (300 MHz, $CDCl_3$): δ 7.88–7.78 (m, 2H), 7.43–7.34 (m, 2H), 7.26 (s, 1H), 3.88 (dd, J=5.0 Hz, J=8.1 Hz, 1H), 3.72 (s, 3H), 3.41 (dd, J=0.7 Hz, J=4.9 Hz, 1H), 3.36 (dd, J=0.7 Hz, J=4.9 Hz, 1H), 3.10 (dd, J=8.4 Hz, J=14.1 Hz, 1H).

Intermediate 7

Preparation of a (+/−)-cis-β-carboline

Trifluoroacetic acid (2.4 mL, 33.2 mmol) was added to a mixture of Intermediate 6 (2.37 g, 5.24 mmol) and piperonal (1.08 g, 7.21 mmol) in toluene (20 mL). The mixture was warmed to 40° C. and stirred for at least 24 hours. The solution was cooled to room temperature, diluted with ethyl acetate (200 mL) and washed with 1N HCl (20 mL), saturated $NaHCO_3$ (2×30 mL), and saturated NaCl (30 mL). The organic phase was dried over anhydrous $Na_2SO_4$, filtered, and the solvent was removed under reduced pressure to provide a brown oily solid. The crude product was purified by column chromatography (silica gel, 0–5% EtOAc/$CH_2Cl_2$) to provide 0.33 g (16.9%) of a pale yellow foam. TLC $R_f$ (5% EtOAc/$CH_2Cl_2$)=0.44; $^1H$ NMR (300 MHz, $CDCl_3$): δ 7.82 (d, J=7.7 Hz, 1H), 7.71 (d, J=7.5 Hz, 1H), 7.41–7.28 (m, 2H), 6.96–6.88 (m, 3H), 6.01 (d, J=0.8 Hz, 2H), 5.19 (m, 1H), 3.99–3.96 (m, 1H), 3.74 (s, 3H), 3.17–3.11 (m, 1H), 2.96 (m, 1H), 2.91–2.84 (m, 1H). The trans carboline was also eluted from the column in impure form: TLC $R_f$ (5% EtOAc/$CH_2Cl_2$)=0.38.

Intermediate 8

Preparation of a (+/−)-cis-2-Chloroacetyl-β-carboline 4

Chloroacetyl chloride (0.09 mL, 1.16 mmol) was added dropwise to a mixture of Intermediate 7 (0.33 g, 0.89 mmol) and triethylamine (0.25 mL, 1.78 mmol) in anhydrous THF (8 mL) at 0° C. under a nitrogen blanket. The resulting mixture was warmed to room temperature and stirred for 0.5 hour. The reaction was quenched with 1N HCl (3 mL) and was concentrated in vacuo. The residue was taken up in $CH_2Cl_2$ (50 mL), then washed with water (2×10 mL) and saturated NaCl (10 mL), and dried over anhydrous $Na_2SO_4$. Filtration and concentration in vacuo provided 0.44 g of a beige foam, which was used without purification in the next step: TLC $R_f$ (3% EtOAc/$CH_2Cl_2$)=0.57.

Example 4

Preparation of (+/−,cis)-10-Benzo[1,3]dioxol-5-yl-7-methyl-5,7,8,10-tetrahydro-5aH-11-thia-7,9a-diazabenzo[β]fluorene-6,9-dione A mixture of crude Intermediate 8 (about 0.39 g, 0.89 mmol), 40% methylamine in water (0.38 mL, 4.45 mmol) in THF (2 mL) was heated at 45° C. under a nitrogen blanket for 15 minutes. The resulting solution was cooled to room temperature, quenched with 0.2 mL concentrated HCl. The THF was removed by vacuum distillation to yield a beige solid. The solid was collected by filtration and reslurried in MeOH. Filtration and washing with MeOH (2×10 mL) provided a cream solid (0.23 g, 63% for two steps); mp 245–266° C.; TLC $R_f$ (5% EtOAc/$CH_2Cl_2$)=0.12; $^1H$ NMR (300 MHz, DMSO-$d_6$): δ 7.88 (dd, J=7.7 Hz, J=14.9 Hz, 2H), 7.42 (dt, J=1.0 Hz, J=7.6 Hz, 1H), 7.35 (dt, J=1.2 Hz, J=7.5 Hz, 1H), 6.87 (s, 1H), 6.76–6.82 (m, 2H), 6.25 (s, 1H), 5.93 (d, J=1.4 Hz, 2H), 4.48 (dd, J=4.1 Hz, J=11.7 Hz, 1H), 4.19 (d, J=16.6 Hz, 1H), 3.96 (d, J=17.2 Hz, 1H), 3.68 (dd, J=4.4 Hz, J=16.3 Hz, 1H), 3.08–2.99 (m, 1H), 2.94 (s, 3H); MS (API) m/z 407 (M+H), 429 (M+Na); $[\alpha]_D^{25°\ C}$=no observed rotation (c=0.51, DMSO). Anal. Calcd. for $C_{22}H_{18}N_2O_4S_1$·$0.5H_2O$; C, 63.60; H, 4.61; N, 6.74; S, 7.72. Found: C, 63.73; H, 4.62; N, 6.71; S, 7.93. The relative stereochemistry of the product was confirmed to be the cis isomer by NOE difference experiments (DMSO-$d_6$): positive NOE enhancements from the C12a proton at 4.48 ppm to the C6 proton at 6.25 ppm.

PREPARATION OF EXAMPLES 5(a) AND 5(b) AND EXAMPLES 6 AND 7

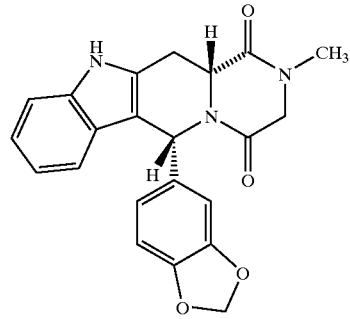

Example 5(a)

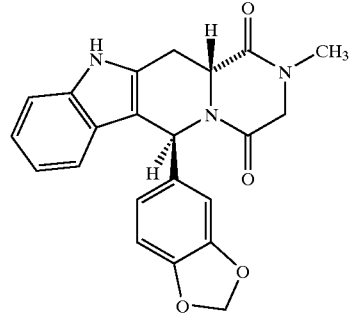

Example 5(b)

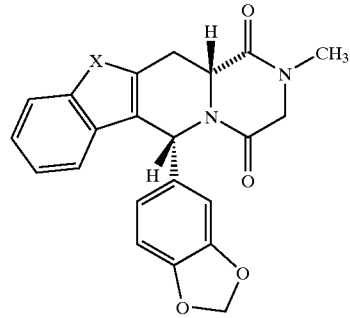

Example 6 (X=O)

Example 7 (X=S)

Examples 5(a), 5(b), 6, and 7 were prepared from the following commercially available compounds:

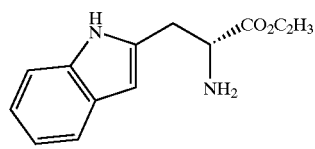

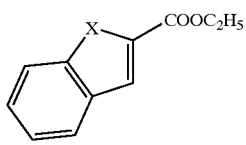

wherein X is NH, O, or S. The synthesis of 2-indolyl alanine, 2-benzofuranyl alanine, and 2-benzothiophenyl alanine starting materials also are disclosed in T. Masquelin et al., *Helv. Chim. Acta*, 77, pages 1395–1411 (1994). The following scheme illustrates one envisioned preparation of Example 5. The compounds of Examples 6 and 7 can be synthesized analogously.

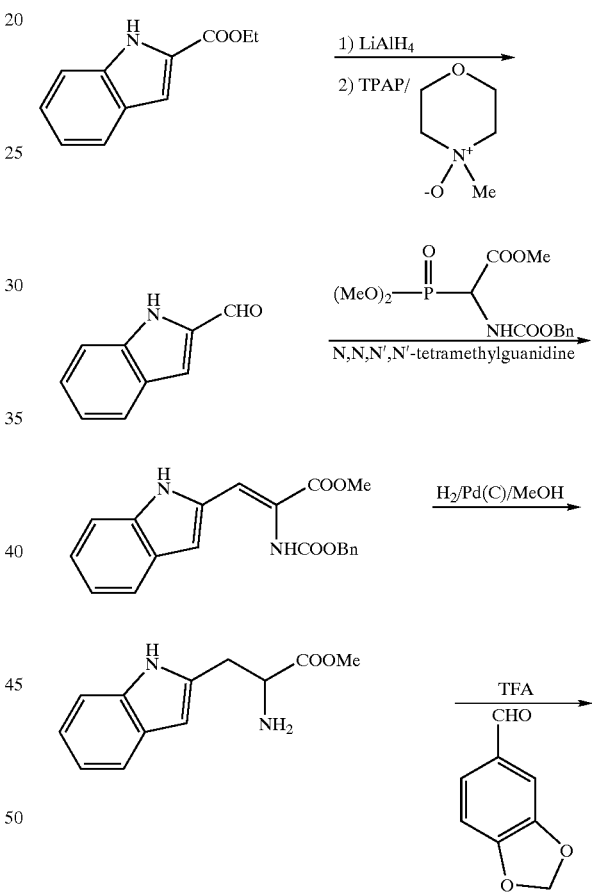

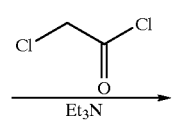

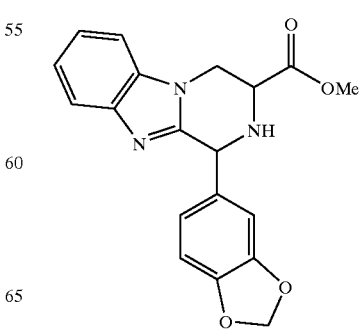

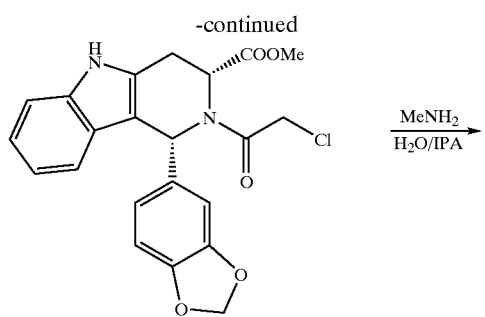

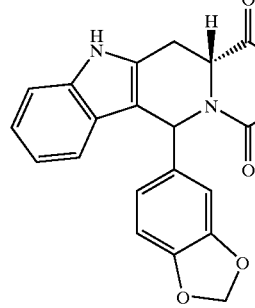

Example 5

The following illustrates another synthetic sequence to Examples 5(a) and 5(b).

PREPARATION OF EXAMPLE 5(a)

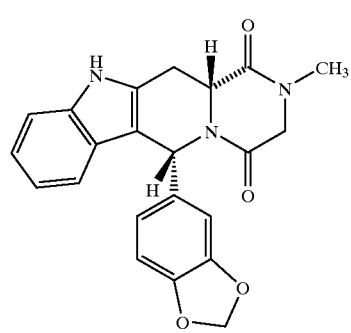

Example 5(a)

Example 5(a) was prepared from the following Intermediates 9 and 11 as depicted in the following synthetic scheme. Intermediates 9 and 10 were prepared from D-isotryptophan, a commercially available compound.

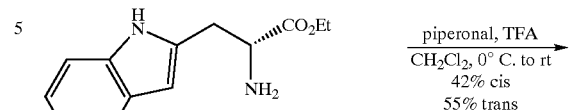

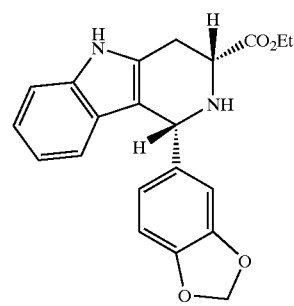

Intermediate 9

+

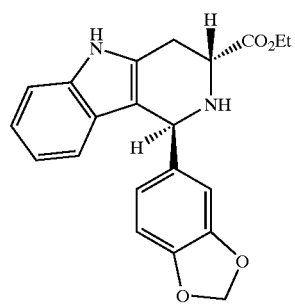

Intermediate 10

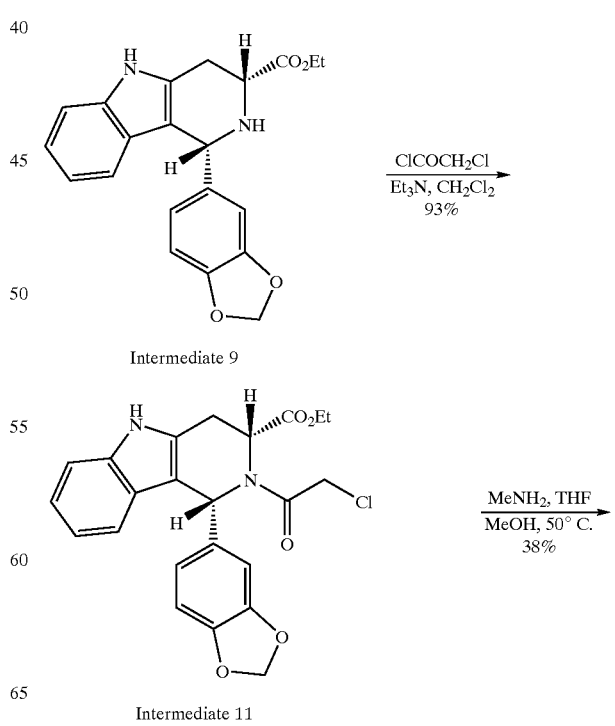

Intermediate 11

-continued

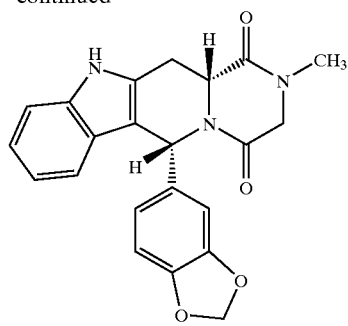

Example 5(a)

Intermediates 9 and 10

Preparation of cis-β-Carboline and trans-β-Carboline

To a solution of D-isotryptophan (0.84 g, 3.6 mmol) and piperonal (0.71 g, 4.8 mmol) in methylene chloride (30 mL) at 0° C. under an argon blanket was added trifluoroacetic acid (0.56 mL, 7.2 mmol). Then the mixture was warmed to room temperature over 4 hours. The resulting pink solution was adjusted to a basic pH with saturated sodium bicarbonate solution. The phases were separated, and the aqueous phase was extracted with methylene chloride (2×50 mL). The combined organic phases were dried over $Na_2SO_4$, then the solvent was removed under reduced pressure to provide a pale pink oil as a residue. The residue was purified by flash column chromatography, eluting with methylene chloride/ethyl acetate (6:1), to provide cis-β-carboline Intermediate 9 as a yellow oil (0.55 g, 42%): TLC $R_f$ (6:1 methylene chloride/ethyl acetate)=0.62; $^1$H NMR (300 MHz, $CDCl_3$): δ 7.90 (s, H), 7.30 (d, J=8.1 Hz, 1H), 7.07 (t, J=7.5 Hz, 1H), 6.94–6.75 (m, 5H), 5.92 (d, J=1.4 Hz, 2H), 5.18 (s, 1H), 4.30–4.19 (m, 2H), 3.97–3.92 (dd, J=6.3, 8.8 Hz, 1H), 3.13–3.09 (m, 2H), 1.31 (t, J=7.1 Hz, 3H) ppm. The latter eluting trans isomer Intermediate 10 also was isolated as a yellow oil (0.73 g, 55%): TLC $R_f$ (6:1 methylene chloride/ethyl acetate)=0.38; $^1$H NMR (300 MHz, $CDCl_3$): δ 8.04 (s, 1H), 7.29 (d, J=8.1 Hz, 1H), 7.12–7.07 (m, 1H), 7.02–6.91 (m, 2H), 6.82–6.72 (m, 3H), 5.91 (d, J=1.6 Hz, 2H), 5.35 (s, 1H), 4.27–4.07 (m, 2H), 3.96–3.92 (dd, J=5.3, 7.2 Hz, 1H), 3.17–3.07 (m, 2H), 2.35 (bs, 1H), 1.27 (t, J=7.1 Hz, 3H) ppm.

Intermediate 11

Preparation of cis-2-Chloroacetyl-β-carboline

Chloroacetyl chloride (0.16 mL, 2.01 mmol) was added to a solution of cis-β-carboline Intermediate 9 (0.55 g, 1.51 mmol) and triethylamine (0.30 mL, 2.15 mmol) in methylene chloride (40 mL) at 0° C. under an argon blanket, after which the resulting mixture was warmed to room temperature over 3 hours. The yellow slurry was dissolved in methylene chloride (50 mL), then washed with water (20 mL) and saturated $NaHCO_3$ solution (20 mL). The organic phase was dried over $Na_2SO_4$, then the solvent was removed under reduced pressure to yield cis-2-chloroacetyl-β-carboline Intermediate 11 as an orange solid which was used without further purification (0.62 g, 93%): TLC $R_f$ (8:1 methylene chloride/ethyl acetate)=0.63.

Example 5(a)

Preparation of (5R,9aR)-5-Benzo(1,3)dioxol-5-yl-8-methyl-5,7,8,9a,10,11-hexahydro-5a,8,11-triaza-benzo[b]fluorane-8,9-dione A solution of Intermediate 11 (0.62 g, 1.41 mmol) and methylamine (3.5 mL, 7.03 mmol, 2 M solution in THF) in methanol (15 mL) was heated at 50° C. under an argon blanket for 16 hours. The resulting solids were isolated by filtration under reduced pressure to provide Example 5(a) as a pale yellow solid (0.207 g, 38%): mp 274–277° C.; TLC $R_f$ (4:1:0.3 methylene chloride/ethyl acetate/methanol)= 0.40; $^1$H NMR (300 MHz, DMSO-$d_6$): δ 11.14 (s, H), 7.45 (d, J=7.8 Hz, 1H), 7.30 (d, J=7.9 Hz, 1H), 7.05–6.99 (dt, J=1.0, 7.5 Hz, 1H), 6.92 (t, J=7.5 Hz, 1H), 6.87 (s, 1H), 6.83 (d, J=1.7 Hz, 1H), 6.71 (d, J=7.7 Hz, 1H), 6.23 (s, 1H), 5.88–5.87 (dd, J=1.0, 3.7 Hz, 2H), 4.51–4.45 (dd, J=4.3, 11.5 Hz, 1H), 4.16 (d, J=17.3 Hz, 1H), 3.92 (d, J=17.2 Hz, 1H), 3.47–3.40 (dd, J=4.7, 16.4 Hz, 1H), 3.32–3.22 (m, 1H), 2.92 (s, 3H) ppm; ESI MS m/z 390 $[C_{22}H_{19}N_3O_4+H]^+$. Anal. Calcd. for $C_{22}H_{19}N_3O_4$: C, 67.86; H, 4.92; N, 10.79. Found: C, 67.53; H, 4.96; N, 10.73. HPLC analysis (Chiralcel OD Column, 250×4.5 mm, Retention Time=12.8 min; 1:1 isopropanol/-hexane; flow=1.00 mL/min; detector 254 nm; temperature ambient) showed one peak, with a purity of 99.5%. The stereochemistry of Example 5(a) was confirmed to be the desired cis isomer by a series of NOE difference experiments: a positive NOE enhancement from the C12a proton at 4.50 ppm to the C6 proton at 6.23 ppm; a positive NOE enhancement from the C6 proton at 6.23 ppm to the C12a proton at 4.50 ppm.

PREPARATION OF EXAMPLE 5(b)

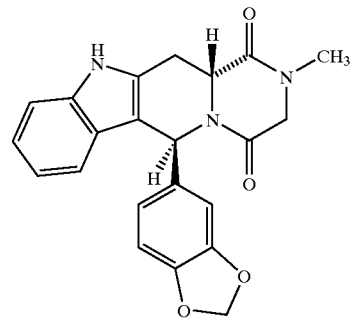

Example 5(b)

Example 5(b) was prepared from the above-described Intermediate 10 as depicted in the following synthetic scheme.

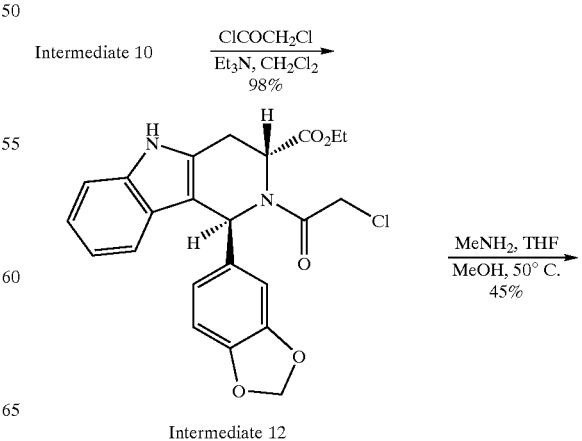

Intermediate 12

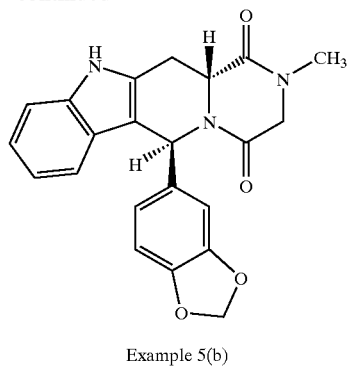

Example 5(b)

Intermediate 12

Preparation of (+)-trans-2-Chloroacetyl-β-carboline

Chloroacetyl chloride (0.21 mL, 2.64 mmol) was added to a solution of Intermediate 10 (0.73 g, 2.00 mmol) and triethylamine (0.36 mL, 2.58 mmol) in methylene chloride (45 mL) at 0° C. under an argon blanket, after which the resulting mixture was warmed to room temperature over 3 hours. The orange solution was dissolved in methylene chloride (50 mL), washed with water (20 mL) and a saturated $NaHCO_3$ solution (20 mL). The organic phase was dried over $Na_2SO_4$, then the solvent was removed under reduced pressure to afford trans-2-chloroacetyl-β-carboline Intermediate 12 as an orange foam, which was used without further purification (0.86 g, 98%): TLC $R_f$ (8:1 methylene chloride/ethyl acetate)=0.48.

Example 5(b)

Preparation of (5S,9aR)-5-Benzo[1,3]dioxol-5-yl-8-methyl-5,7,8,9a,10,11-hexahydro-5a,8,11-triaza-benzo[b]fluorene-8,9-dione A solution of trans-2-chloroacetyl-β-carboline Intermediate 12 (0.86 g, 1.95 mmol) and methylamine (9.8 mL, 19.5 mmol, 2 M solution in THF) in methanol (15 mL) was heated at 50° C. under an argon blanket for 16 hours. The resulting solution was cooled to room temperature, then concentrated under reduced pressure to provide an orange foam. The residue was purified by flash column chromatography, eluting with methylene chloride/ethyl acetate/methanol (4:1:0.3) to provide a yellow foam. The foam was slurried in diethyl ether and the solids were collected by vacuum filtration to provide Example 5(b) as an off-white solid (0.345 g, 45%): mp 274–277° C.; TLC $R_f$ (4:1:0.3 methylene chloride/ethyl acetate/methanol)=0.30; $^1$H NMR (300 MHz, DMSO-$d_6$): δ 11.19 (s, 1H), 7.36 (d, J=8.0 Hz, 1H), 7.08–7.00 (m, 2H), 6.91–6.80 (m, 4H), 6.68 (d, J=8.1 Hz, 1H), 5.97 (d, J=4;2 Hz, 1H), 4.23 (d, J=17.5 Hz, 1H), 4.15–4.09 (dd, J=4.6, 11.2 Hz, 1H), 4.03 (d, J=17.5 Hz, 1H), 3.36–3.10 (m, 3H), 2.84 (s, 3H) ppm; ESI MS m/z 390 [$C_{22}H_{19}N_3O_4$+H]$^+$. Anal. Calcd. for $C_{22}H_{19}N_3O_4$: C, 67.86; H, 4.92; N, 10.79. Found: C, 67.49; H, 4.95; N, 10.68. HPLC analysis (Chiralcel OD Column 250×4.5 mm, Retention Times=8.5 and 10.9 min; 1:1 isopropanol/hexane; flow=1.00 mL/min; detector 254 nm; temperature ambient) showed two peaks, with a ratio of 5:95, respectively, and with a total purity of 100.0%. The stereochemistry of Example 5(b) was confirmed to be the desired trans isomer by a series of NOE difference experiments: no NOE enhancement from the C12a proton at 4.40 ppm to the C6 proton at 7.08 ppm; no NOE enhancement from the C6 proton at 7.08 ppm to the C12a proton at 4.40 ppm.

PREPARATION OF EXAMPLE 8

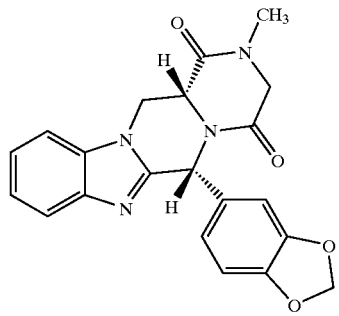

Example 8

The envisioned synthesis of the Example 8 benzimidizole utilizes the same sequence as in the synthesis of Examples 5–7 beginning with esterification of known Intermediate 13 amino acid in methanol catalyzed by sulfuric acid.

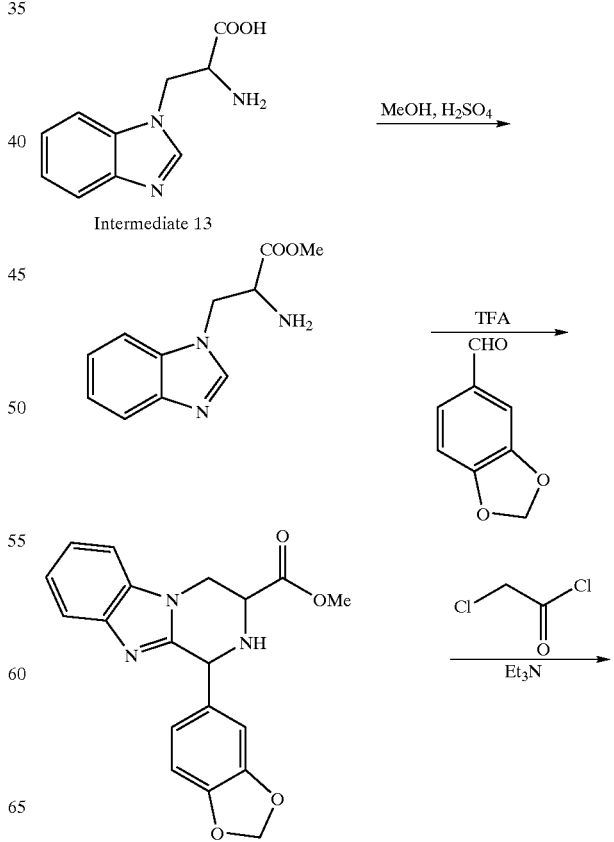

-continued

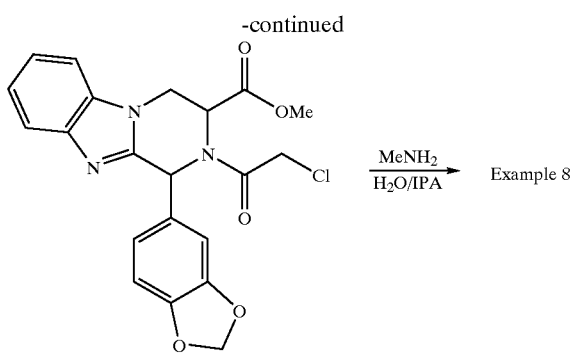

MeNH₂ / H₂O/IPA → Example 8

PREPARATION OF EXAMPLE 9

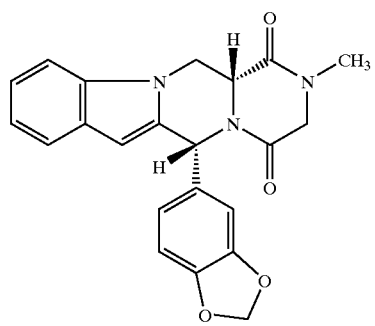

Example 9

Example 9 can be prepared from Intermediate 14, a 1-indolyl alanine described in D. Ranganathan et al., *Tetrahedron Lett.*, 23(27), pages 2789–2792 (1982). The same synthetic sequence used to manufacture Example 8 can be utilized in the synthesis of Example 9.

Intermediate 14

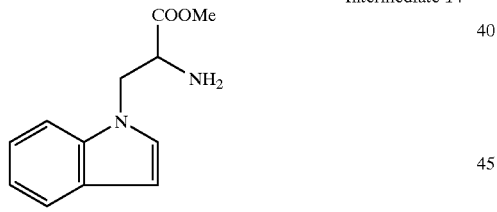

PREPARATION OF EXAMPLE 10

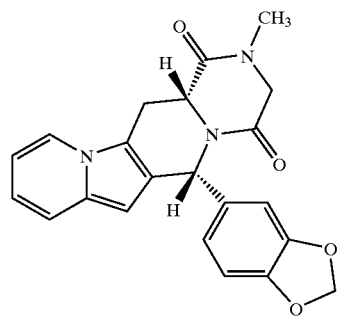

Example 10

Synthesis of indolizine Example 10 from amino ester Intermediate 15 utilizes the same synthetic scheme as Example 8. Intermediate 15 is prepared from known aldehyde Intermediate 16 by use of an appropriate Wittig reaction followed by catalytic hydrogenation of the resulting alkene.

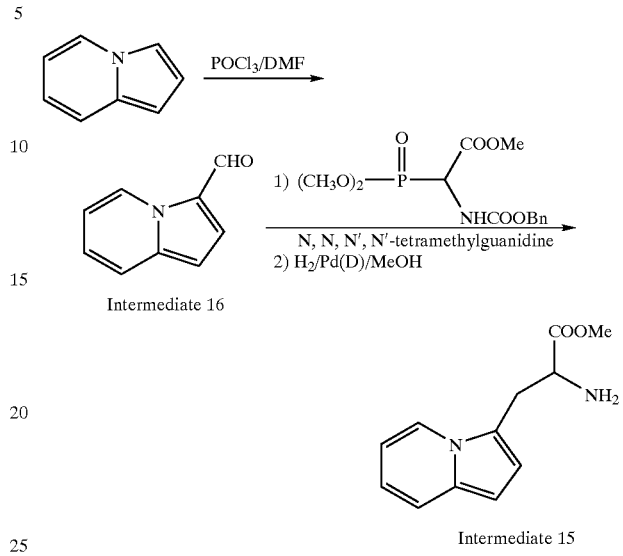

Intermediate 16

Intermediate 15

PREPARATION OF EXAMPLES 11 AND 12

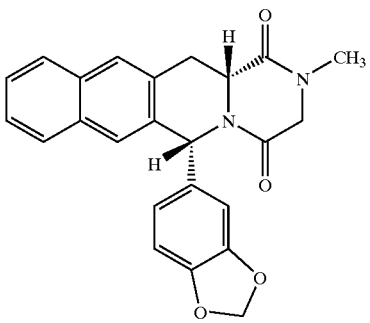

Example 11

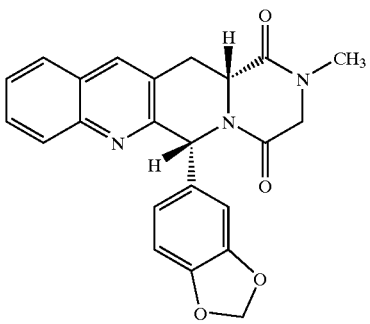

Example 12

Examples 11 and 12 were prepared from the following Intermediates 17 and 18 by the same procedure utilized to prepare Example 8.

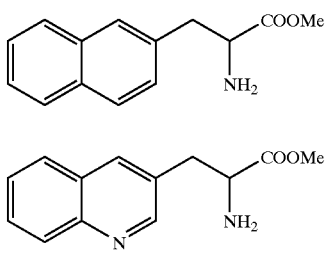

Intermediate 17

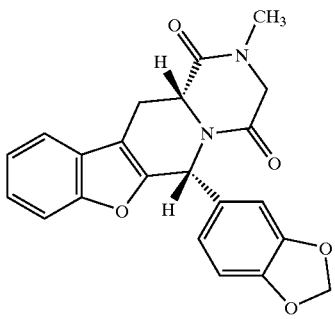

Intermediate 18

The following compound, Example 13, can be prepared by a sequence similar to the preparation of Examples 1–12:

Example 13

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 μM, and preferably less than about 25 μM, and more preferably less than about 15 μm. The compounds of the present invention typically exhibit an $IC_{50}$ value against recombinant human PDE5 of less than about 1 μM, and often less than about 0.05 μM. To achieve the full advantage of the invention, a present PDE5 inhibitor has an $IC_{50}$ of about 0.1 nM to about 15 μM.

The production of recombinant human PDEs and the $IC_{50}$ determinations can be accomplished by well-known methods in the art. Exemplary methods are described as follows:

Expression of Human PDEs
Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2–54 deposited on Aug. 31, 1998 with the American Type Culture Collection, Manassas, Va., under accession number ATCC 74465. Transformed host cells were grown in 2× SC-leu medium, pH 6.2, with trace metals, and vitamins. After 24 hours, YEP medium-containing glycerol was added to a final concentration of 2× YET/3% glycerol. Approximately 24 hr later, cells were harvested, washed, and stored at −70° C.

Human Phosphodiesterase Preparations
Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 μL reaction mixture containing (final concentrations) 40 mM Tris HCl (pH 8.0), 1 μM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) μg of Crotalus atrox venom then was added, and the incubation was continued for 3 minutes (15 minutes total). The reaction was stopped by addition of 200 μL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 μM $ZnSO_4$). Cells were lysed in a Microfluidizer® (Microfluidics Corp.) using nitrogen at 20,000 psi. The lysate was centrifuged and filtered through 0.45 μm disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM $MgCl_2$, 0.25 mM DTT, 10 μM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 μM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 μM $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 μmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 µg/ml 5'-Nucleotidase, 1 mM EGTA, and 0.15 µM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 µM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 500 nM. An in vitro test using Example 1, a representative compound of the invention, gave $IC_{50}$ versus PDE5 of 2.3 nM. Examples 4, 5(a), and 5(b) demonstrated an $IC_{50}$ versus PDE5 of 555 nM, 338 nM, and 125 nM, respectively.

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

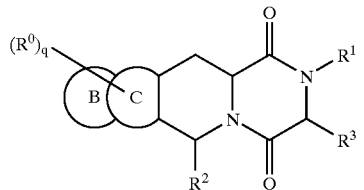

wherein $R^0$, independently, is selected from the group consisting of halo and $C_{1-6}$alkyl;

$R^1$ is selected from the group consisting of hydrogen, $C_{1-6}$alkyl, $C_{2-6}$alkenyl, $C_{2-6}$alkynyl, halo-$C_{1-6}$alkyl, $C_{3-8}$cycloalkyl, $C_{3-8}$cycloalkyl$C_{1-3}$alkyl, and aryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

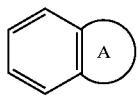

wherein the fused ring A is a 5- or 6-membered ring, saturated or partially or fully unsaturated, and comprises carbon atoms and optionally one or two heteroatoms selected from oxygen, sulfur, and nitrogen, said optional substituents selected from the group consisting of halo, $C_{1-3}$alkyl, $OR^a$, $CO_2R^a$, halomethyl, halomethoxy, cyano, nitro, and $N(R^a)_2$;

$R^3$ is hydrogen or $C_{1-3}$alkyl;

rings B and C form an optionally substituted fused ring structure selected from the group consisting of

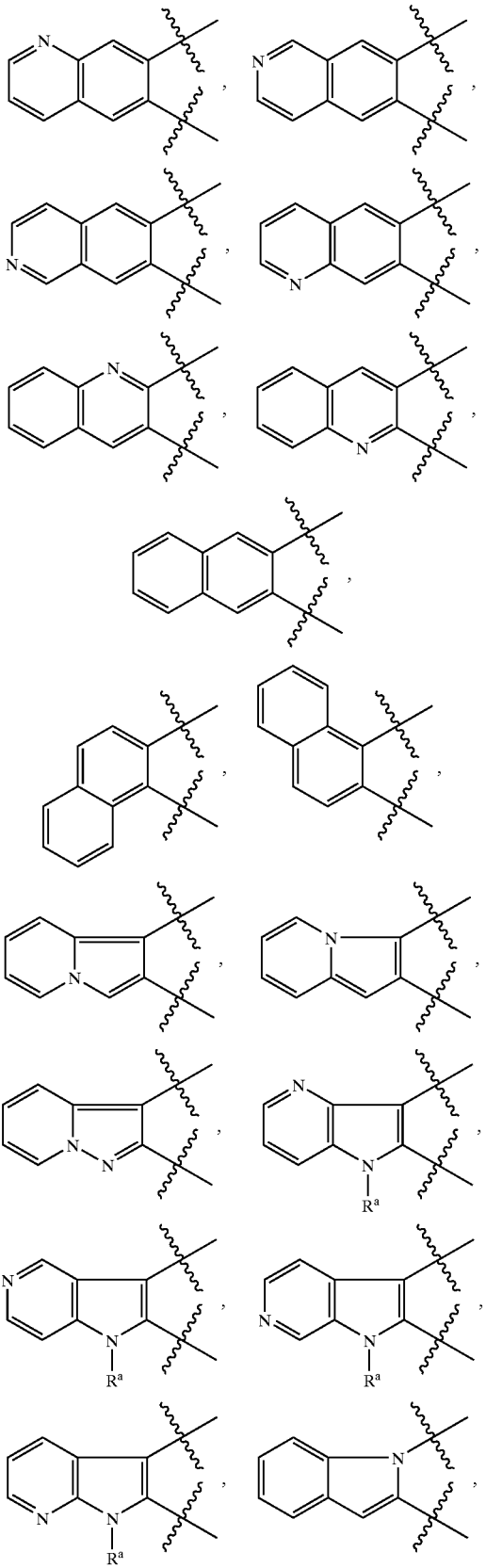

-continued

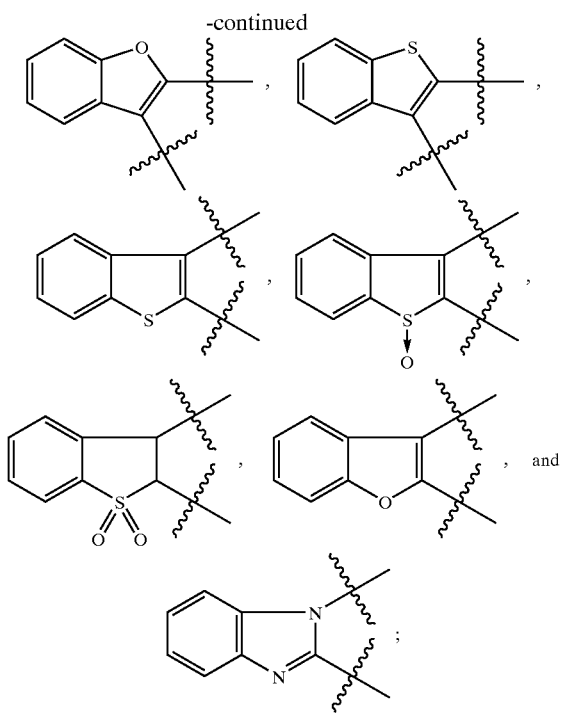

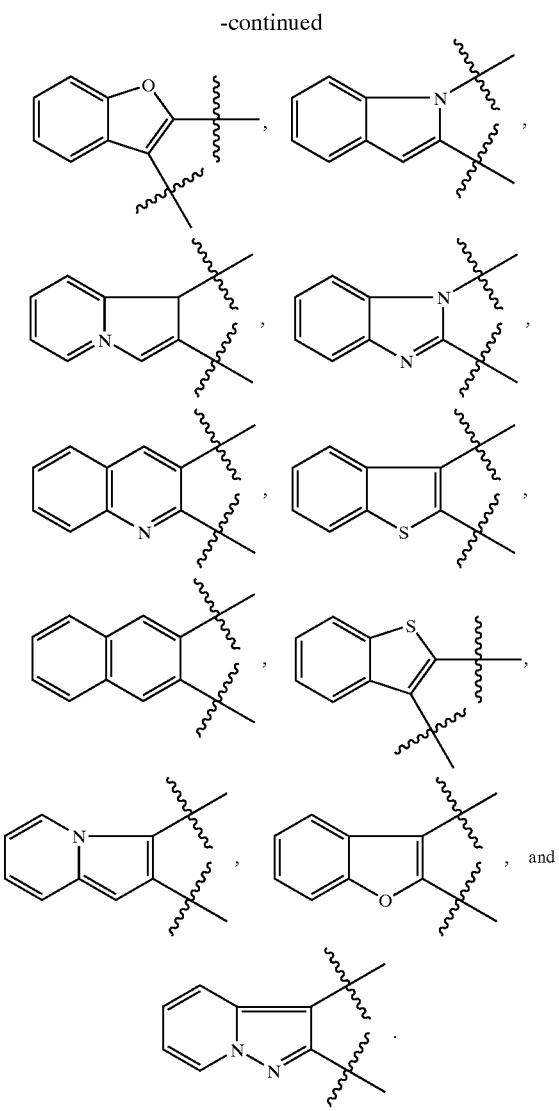

R$^a$ is selected from the group consisting of hydrogen, C$_{1-6}$alkyl, C$_{3-8}$cycloalkyl, aryl, arylC$_{1-3}$alkyl, C$_{1-3}$alkylenearyl;

q is 0, 1, 2, 3, or 4; or a pharmaceutically acceptable salt or hydrate thereof.

2. The compound of claim 1 represented by the formula

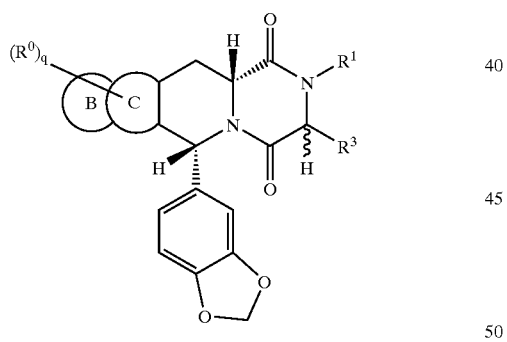

or a pharmaceutically acceptable salt or hydrate thereof.

3. The compound of claim 1 wherein R$^1$ is methyl.

4. The compound of claim 1 wherein R$^3$ is hydrogen.

5. The compound of claim 1 wherein rings B and C form an optionally substituted fused ring structure selected from the group consisting of

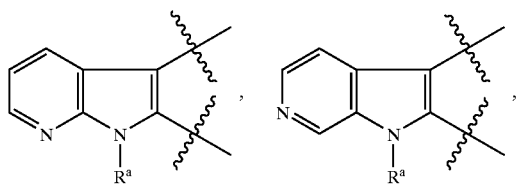

6. The compound of claim 1 wherein R$^2$ is an optionally substituted bicyclic ring selected from the group consisting of naphthalene, indene, benzoxazole, benzothiazole, benzisoxazole, benzimidazole, quinoline, indole, benzothiophene, and benzofuran.

7. The compound of claim 1 wherein R$^2$ is

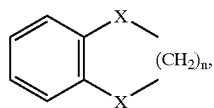

wherein n is an integer 1 or 2, and X, independently, are C(R$^a$)$_2$, O, S, or NR$^a$.

8. The compound of claim 1 wherein R$^2$, substituted or unsubstituted, is selected from the group consisting of

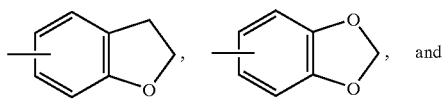

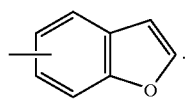
9. The compound of claim 8 wherein $R^2$ is substituted with a substituent selected from the group consisting of halogen, $C_{1-3}$alkyl, $OR^a$, $CO_2R^a$, halomethyl, halomethoxy, cyano, nitro, and $N(R^a)_2$.
10. A compound selected from the group consisting of
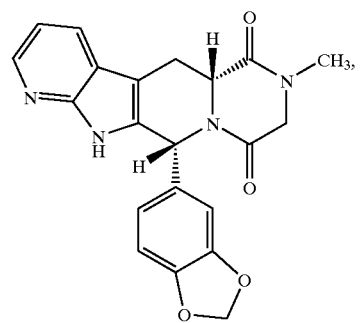
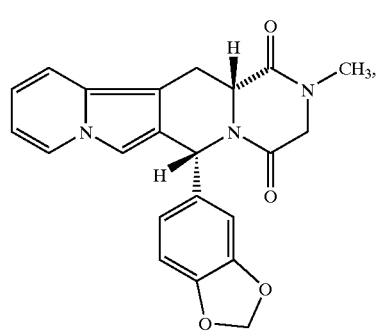
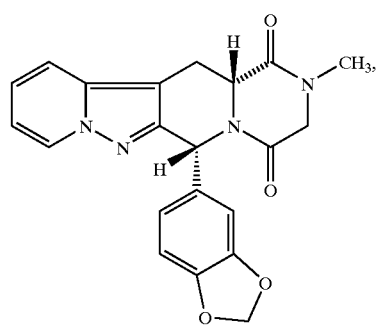
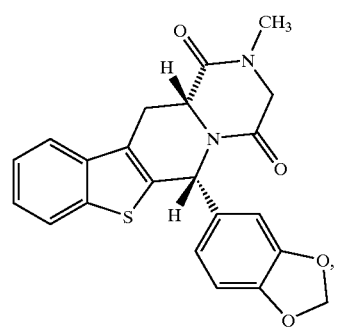
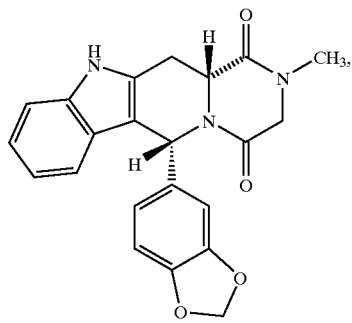
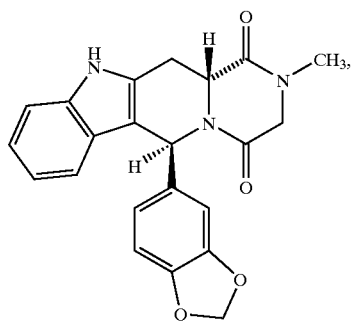
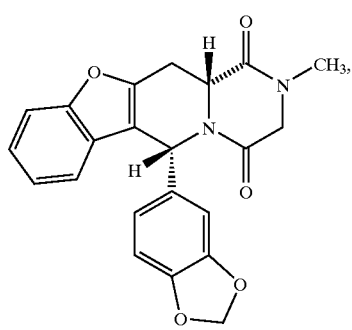
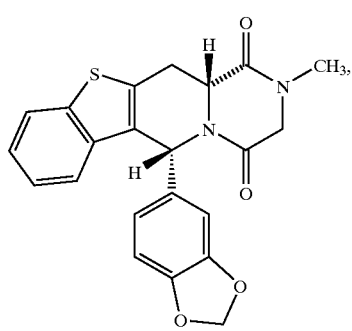
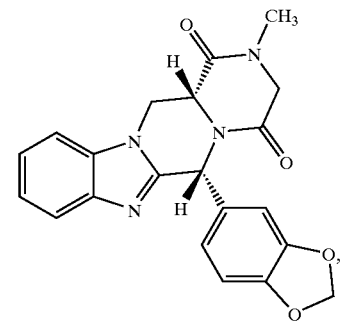

-continued

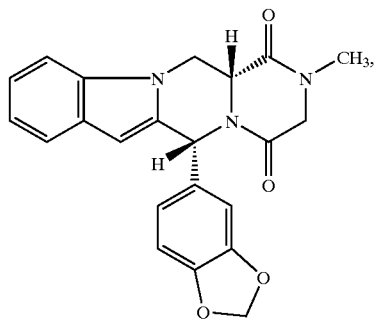

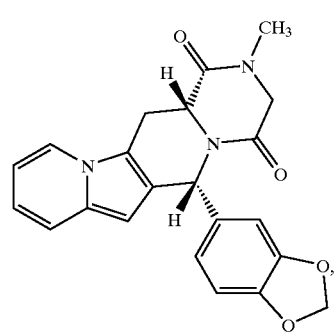

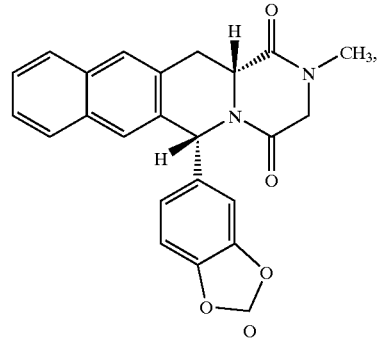

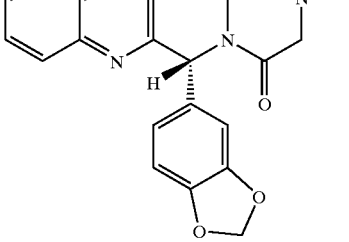

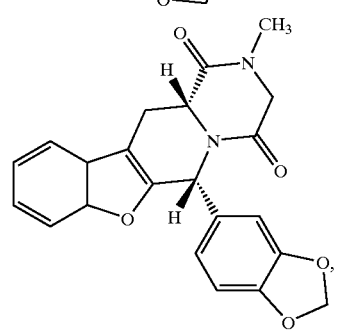

or a pharmaceutically acceptable salt or hydrate thereof.

11. A pharmaceutical composition comprising a compound of claim 1, together with a pharmaceutically acceptable diluent or carrier.

12. A method of treating a male or female animal for male erectile dysfunction or female arousal disorder comprising administering to said animal an effective amount of a pharmaceutical composition comprising a compound of claim 1, together with a pharmaceutically acceptable diluent or carrier.

13. The method of claim 12 wherein the pharmaceutical composition is administered orally.

14. A compound having a formula

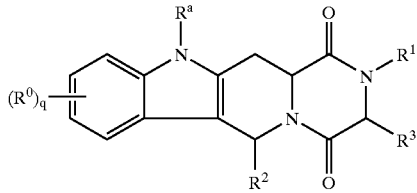

wherein $R^0$, independently, is selected from the group consisting of halo and $C_{1-6}$alkyl;

$R^1$ is selected from the group consisting of hydrogen, $C_{1-6}$alkyl, $C_{2-6}$alkenyl, $C_{2-6}$alkynyl, halo-$C_{1-6}$alkyl, $C_{3-8}$cycloalkyl, $C_{3-8}$cycloalkyl$C_{1-3}$alkyl, and aryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

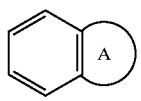

wherein the fused ring A is a 5- or 6-membered ring, saturated or partially or fully unsaturated, and comprises carbon atoms and optionally one or two heteroatoms selected from oxygen, sulfur, and nitrogen, said optional substituents selected from the group consisting of halo, $C_{1-3}$alkyl, $OR^a$, $CO_2R^a$, halomethyl, halomethoxy, cyano, nitro, and $N(R^a)^2$;

$R^3$ is hydrogen or $C_{1-3}$alkyl;

$R^a$ is selected from the group consisting of hydrogen, $C_{1-6}$alkyl, $C_{3-8}$cycloalkyl, aryl, aryl$C_{1-3}$alkyl, $C_{1-3}$alkylenearyl.

q is 0, 1, 2, 3, or 4;

or a pharmaceutically acceptable salt or hydrate thereof.

* * * * *

UNITED STATES PATENT AND TRADEMARK OFFICE
CERTIFICATE OF CORRECTION

PATENT NO. : 6,903,099 B2
DATED : June 7, 2005
INVENTOR(S) : Orme et al.

It is certified that error appears in the above-identified patent and that said Letters Patent is hereby corrected as shown below:

Column 1,
Line 44, "haloC$_{1-6}$-alkyl" should be -- haloC$_{1-6}$alkyl --.
Line 45, "aryl-C$_{1-3}$alkyl" should be -- arylC$_{1-3}$alkyl --.

Column 2,
Line 64, "arylC$_{1-3}$-alkyl" should be -- arylC$_{1-3}$alkyl --.

Column 3,
Line 6, "C$_6$-C$_{16}$bicyclic" should be -- C$_6$-C$_{16}$ bicyclic --.

Column 9,
Line 25, "lipophilic-solvents" should be -- lipophilic solvents --.

Column 13,
Line 34, "306" should be -- 300 --.
Line 63, "(+/-,cis)" should be -- (+/-, cis) --.

Column 14,
Line 24, "C$_{21}$H$_{18}$N$_4$O$_4$.0.7" should be -- C$_{21}$H$_{18}$N$_4$O$_4$·0.7 --.

Column 18,
Line 62, "C$_{22}$H$_{18}$N$_2$O$_4$S$_1$.0.5" should be -- C$_{22}$H$_{18}$N$_2$O$_4$S$_1$·0.5 --.

Column 21,
Lines 12-30, delete duplicate structure.

UNITED STATES PATENT AND TRADEMARK OFFICE
CERTIFICATE OF CORRECTION

PATENT NO.    : 6,903,099 B2
DATED         : June 7, 2005
INVENTOR(S)   : Orme et al.

It is certified that error appears in the above-identified patent and that said Letters Patent is hereby corrected as shown below:

Column 25,
Line 56, "(d, J=4;2" should be -- (d, J=4.2 --.

Column 31,
Line 47, "halo-$C_{1-6}$alkyl" should be -- halo$C_{1-6}$alkyl --.

Column 38,
Line 31, "halo-$C_{1-6}$alkyl"should be -- halo$C_{1-6}$alkyl --.

Signed and Sealed this

Sixth Day of December, 2005

JON W. DUDAS
*Director of the United States Patent and Trademark Office*